US00RE38811E

(19) United States
(12) Reissued Patent
Knutson

(10) Patent Number: US RE38,811 E
(45) Date of Reissued Patent: Oct. 4, 2005

(54) DENTAL TRAY SPACER

(75) Inventor: Eric J. Knutson, Granite Bay, CA (US)

(73) Assignee: 3M Innovative Properties Company, St. Paul, MN (US)

(21) Appl. No.: 09/482,448

(22) Filed: Jan. 12, 2000

Related U.S. Patent Documents

Reissue of:
(64) Patent No.: 5,707,235
Issued: Jan. 13, 1998
Appl. No.: 08/415,493
Filed: Apr. 3, 1995

(51) Int. Cl.[7] ..... A61C 11/00
(52) U.S. Cl. ..... 433/213; 433/214; 433/215
(58) Field of Search ..... 433/213, 214, 433/215, 34, 37, 216

(56) References Cited

U.S. PATENT DOCUMENTS

| | | | | |
|---|---|---|---|---|
| 2,196,505 | A | 4/1940 | Morton | 433/213 |
| 2,963,786 | A | 12/1960 | Browning | 433/37 |
| 3,073,300 | A | 1/1963 | Berghash | 128/136 |
| 3,218,374 | A | 11/1965 | Perbohner et al. | 433/34 |
| 3,247,846 | A | 4/1966 | Fansler | 128/136 |
| 3,379,193 | A | 4/1968 | Monaghan | 128/24 |
| 3,380,446 | A | 4/1968 | Martin | 128/24 |
| 3,404,056 | A | 10/1968 | Baldwin | 156/61 |
| 3,527,219 | A | 9/1970 | Greenberg | 128/260 |
| 3,624,909 | A | 12/1971 | Greenberg | 433/80 |
| 3,688,406 | A | 9/1972 | Porter et al. | 433/217.1 |
| 4,044,762 | A | 8/1977 | Jacobs | 128/136 |
| 4,063,552 | A | 12/1977 | Going et al. | 128/136 |
| 4,173,505 | A | 11/1979 | Jacobs | 433/89 |
| 4,226,593 | A | 10/1980 | Cohen et al. | 433/217 |
| 4,401,616 | A | 8/1983 | Wagner | 264/138 |
| 4,560,351 | A | 12/1985 | Osborne | 433/80 |
| 4,609,350 | A | 9/1986 | Krause | 433/7 |
| 4,657,508 | A | 4/1987 | Dellinger | 433/24 |
| 4,741,700 | A | 5/1988 | Barabe | 433/229 |
| 4,861,268 | A | 8/1989 | Garay et al. | 433/229 |
| 4,968,251 | A | 11/1990 | Darnell | 433/216 |
| 4,978,298 | A | 12/1990 | Eliasz | 433/213 |

(Continued)

FOREIGN PATENT DOCUMENTS

GB 2 002 637 2/1979

OTHER PUBLICATIONS

Freedman, George A., "Foam Insert Improves Whitening Tray", Dentistry Today, vol. 9, No. 4, May 1990, p. 7.*

Clinical Research Associates, "Clinically Successful Uses of Vacuum Formed Plastics,"Newsletter, vol. 14, Issue 6, Jun. 1990, p. 2.

Feinman, Ronald A., "Matrix Vital Bleaching: A Review", Esthetic Dentistry Update, vol. 2, No. 3, Jun. 1991, pp. 42–48.

Haywood, Van Benjamin, "Overview and Status of Mouthguard Bleaching", Journal of Esthetic Dentistry, vol. 3, No. 5, Sep./Oct. 1991, pp. 157–161.

Haywood, Van B. et al., "Efficacy of Foam Liner in 10% Carbamide Peroxide Bleaching Technique", Quintessence International, vol. 24, No. 9, 1993, pp. 663–666.

Reality, "Bleaching–Patient Administered", Reality, vol. 5, No. 2, 1990, pp. 155–158.

*Primary Examiner*—John J. Wilson
(74) *Attorney, Agent, or Firm*—James D. Christoff

(57) ABSTRACT

A convenient dental tray spacer for use in forming a thin reservoir space between teeth and a dental tray, during tray fabrication. Shim (10) segments are connected by small links (12) to form a spacer (16). The lengths of the links are readily variable. Retention to the teeth is provided by adhesive on rear adhesive surfaces (22). Alternatively, an elastic loop (24) can retain a spacer (16'). Spacer (16), or spacer (16'), remain on the teeth while the dental tray is formed, and then is pulled free from inside the formed dental trays.

34 Claims, 2 Drawing Sheets

U.S. PATENT DOCUMENTS

| | | | | |
|---|---|---|---|---|
| 4,983,381 | A | 1/1991 | Torres Zaragoza | 433/215 |
| 4,990,089 | A | 2/1991 | Munro | 433/215 |
| 5,009,885 | A | 4/1991 | Yarborough | 433/215 |
| 5,049,077 | A | 9/1991 | Goldin et al. | 433/229 |
| 5,087,202 | A | 2/1992 | Krenkel | 433/215 |
| 5,098,303 | A | 3/1992 | Fischer | 433/215 |
| RE34,196 | E | 3/1993 | Munro | 433/215 |
| 5,234,342 | A | 8/1993 | Fischer | 433/215 |
| 5,310,563 | A | 5/1994 | Curtis et al. | 433/215 |
| 5,323,787 | A | 6/1994 | Pratt | 433/37 |
| 5,326,685 | A | 7/1994 | Gaglio et al. | 433/215 |
| 5,356,291 | A | 10/1994 | Darnell | 433/216 |
| 5,376,006 | A | 12/1994 | Fischer | 433/215 |
| 5,409,631 | A | 4/1995 | Fischer | 252/186.25 |
| 5,562,449 | A | 10/1996 | Jacobs et al. | 433/215 |
| 5,573,399 | A | 11/1996 | McClintock, II | 433/80 |
| 5,575,654 | A | 11/1996 | Fontenot | 433/215 |
| 5,575,655 | A | 11/1996 | Darnell | 433/216 |
| 5,702,251 | A | 12/1997 | McClintock, II | 433/80 |
| 5,725,843 | A | 3/1998 | Fischer | 433/215 |
| 5,746,598 | A | 5/1998 | Fischer | 433/216 |
| 5,759,037 | A | 6/1998 | Fischer | 433/215 |
| 5,759,038 | A | 6/1998 | Fischer | 433/215 |
| 5,770,105 | A | 6/1998 | Fischer | 433/215 |
| 5,842,860 | A | 12/1998 | Funt | 433/80 |
| 5,863,202 | A | 1/1999 | Fontenot et al. | 433/215 |

* cited by examiner

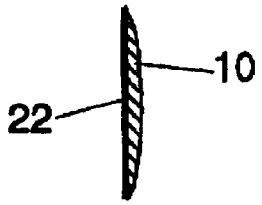
Fig. 5-A
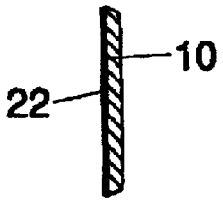
Fig. 5-B
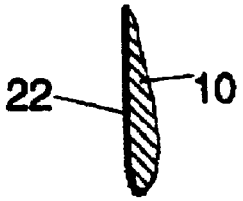
Fig. 5-C
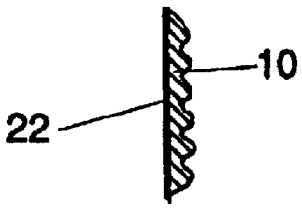
Fig. 5-D
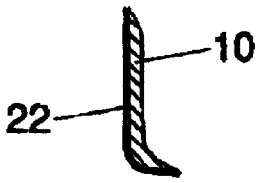
Fig. 5-E
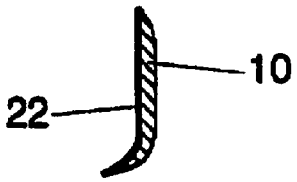
Fig. 5-F
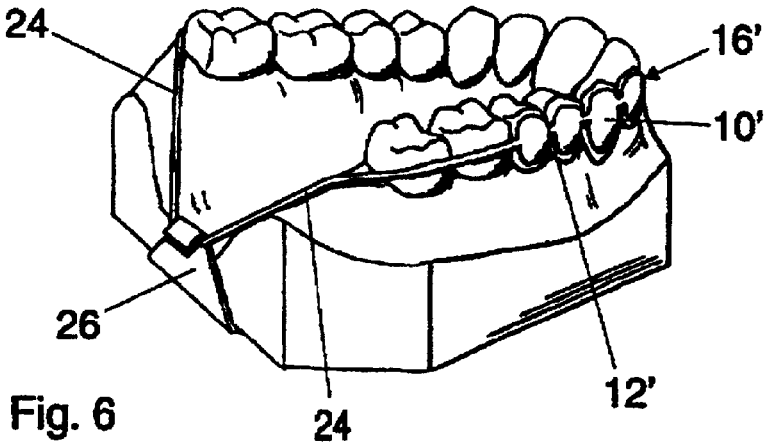
Fig. 6

DENTAL TRAY SPACER

Matter enclosed in heavy brackets [ ] appears in the original patent but forms no part of this reissue specification; matter printed in italics indicates the additions made by reissue.

BACKGROUND—FIELD OF THE INVENTION

This invention relates to medicine and dentistry, specifically to an improved method and apparatus for fabricating custom dental treatment trays for applying treatment agents to the teeth and/or gingiva.

BACKGROUND—DESCRIPTION OF PRIOR ART

Custom dental treatment trays are used to hold tooth whitening or bleaching gels, fluoride, topical anesthetics, antibiotics, antihistamines, medications, and other such treatment agents, closely against the surfaces of the teeth and/or gingiva for extended times. Dental trays typically are made by tightly suctioning softened elastomeric sheets of stock tray material onto plaster models of the patient's dental arches. Excess tray material is then trimmed away to achieve the desired tray shape. Dental trays are most effective when fabricated with slight spacing created between the surfaces of the teeth and the tray material. This provides room, or a reservoir, for the treatment agents. Without a reservoir space, the tray material itself tightly contacts the broad surfaces of the teeth, and the treatment agents tend to be displaced. When this occurs, the beneficial effects of the treatment agents are reduced, and the treatment time, the amount of treatment agents required, and irritational side effects are increased.

There is a problem with creating the reservoir space under the dental trays, however, and that is the considerable time it requires for dental personnel. Cost is also a factor for some techniques.

The most widely used dental tray spacing technique involves manually painting a liquid spacer material, such as thick fingernail polish, onto the appropriate areas of the patient's teeth, or models of their teeth, prior to forming the trays. The depth of the paint itself forms the tray space. Typically, only one coat is painted on, although this forms a relatively thin space, and it must be allowed to dry before the dental tray may be fabricated. A border area around the circumference of the tooth remains unspaced, in order to seal off the reservoir area from saliva, and to retain the treatment agent. The first disadvantage to this technique is that several minutes are required to apply one coat of spacer paint, plus about twenty minutes for drying. The second disadvantage is that multiple coats are needed to achieve an ideal thickness for the reservoir space. Since that would require excessive time, a minimally adequate reservoir depth from just one coat is usually tolerated as better than none. A third disadvantage is that the thin spacing is not readily apparent when inspecting the tray visually. Thus the dentist or patient, who is to purchase the spaced dental tray, must rely on the word of the maker that is was actually spaced. This is a disincentive for laboratory and dental personnel to accept the inconvenience and cost of properly spacing the dental trays.

A similar technique involves manually painting viscous light-cured spacing resin over the teeth surfaces, instead of fingernail polish. Again, it is not applied to the border area, so that a seal may be created for retaining the treatment agent over the treatment surface, and to seal out saliva. It creates a more ideal thickness of reservoir space with a single coat. However, it still has the disadvantage of [requiting] *requiring* several minutes to paint on the teeth. Then, the resin is hardened with two minutes exposure to a special curing lamp. Another disadvantage is the considerable cost of the special curing lamp apparatus. To avoid that expense, many dentists cure with their existing intraoral curing lamps instead. Unfortunately, these require a twenty to forty second exposure time per tooth, which more than doubles the time required to cure the resin spacing medium, and these lamps have higher operational costs. The light-cured resin itself is also costly.

Another technique involves molding clay-like material onto the surfaces of the teeth. Again, the border seal area is left unspaced. This technique requires some sculpting skill, and still greater application time. It is not commonly used.

Another technique, described as the primary embodiment in U.S. Pat. No. 5,356,291 to Darnell (1994), involves covering the entire inner surface of the tray with a sheet of open or closed cell foam, or a sheet of fibrous absorbent material. This does not create an effective border seal, so it is somewhat ineffective in retaining and restricting the treatment agent to the area immediately over the teeth. Instead, the treatment agent is permitted to dissipate in concentration and effectiveness over the treatment surfaces, while saliva increasingly soaks into its place. At the same time, the treatment agent may flow out over the gingiva or root areas, where it may cause irritation. This is especially true for tooth bleaching gels. A second disadvantage is that the foam or fiber quickly accumulates heavy bacteria plaque and debris, and begins to look and smell badly. Repeated cleaning the foam or fiber tends to destroy it, as it is somewhat fragile. The foam or fiber also deteriorates and oxidizes more quickly than the dental tray material that backs it.

A secondary embodiment of Darnell (1994) utilizes foam or fiber material segments to act as treatment agent reservoirs between the tray and individual teeth. The disadvantage is that the construction is tedious, and the resulting tray is difficult to clean. Darnell does not teach removable shims for dental tray spacing.

A tertiary embodiment of Darnell (1994) involves creating the space between the dental tray and the teeth by abrading or sandblasting away some of the inner surface dental tray material from the formed dental tray. The disadvantages of this technique are that costly sandblasting apparatus is required, that skillful, highly attentive workmanship is required to accurately cut away dental tray material, and that the dental tray material is somewhat weakened over the indentation/reservoir site. Thicker, less comfortable, tray material is required, than for techniques which do not thin the tray.

Another technique, reported in U.S. Pat. No. 5,326,685 to Gaglio et al. (1994), utilizes an impervious flexible backing material over an open-cell foam, to create a reservoir for treatment agents. An additional reservoir is formed by sealing the borders of the foam to the backing material, thus creating a space between them. Disadvantages of this technique include complex fabrication, additional steps being required to load treatment agents into the reservoir spaces, the inability to seal the treatment surfaces from saliva, the inability to seal or restrict the treatment agents to the treatment surfaces, and difficulty cleaning the open cell foam.

Millions of dental trays are currently in use, most for bleaching teeth. Many are fabricated without spacing built in at all, because of the cost and inconvenience to the dental personnel to make spaced trays. But unspaced dental trays waste the time and money of patients who attempt to utilize them. The resilient dental tray material squeezes the treatment agents away from the desired location, reducing the effectiveness and efficiency. Bleaching sessions typically last several hours of time, and the bleaching agents are costly. The process is further undetermined because the displaced bleach increasingly contacts, and may irritate, the gingiva and root areas of the teeth.

A dental tray spacer has not been produced to date because it is not obvious how to connect shim segments for convenient mounting on the wide variety of dental arches, with their differences in distances between tooth centers, tooth sizes, shapes, misalignments, gaps and rotations.

OBJECTS AND ADVANTAGES

Accordingly, several objects and advantages of the present invention are:

(a) to provide an improved method for forming reservoir spaces under dental trays, for treating teeth with treatment agents, which produces results which are superior to the results heretofore known to the art;

(b) to provide a spacer comprising multiple connected shims, each of which mount on individual teeth, such that several teeth of a dental arch of teeth may be quickly shimmed with a single spacer;

(c) to provide a spacer which is shaped to form adequate reservoir spaces under dental trays, as the trays are formed, wherein such spaces can readily receive and hold treatment agents;

(d) to provide a spacer shaped to substantially cover surfaces of teeth, leaving a circumferential area of the tooth surface uncovered, and unspaced, such that the formed tray rests directly against the circumference of the tooth, thus enclosing a central, spaced, reservoir area which can retain treatment agents, while restricting oral fluids from treated tooth surfaces;

(e) to provide a spacer which is somewhat deformable, to compensate for variations in the size, shape and spacing between individual teeth of a dental arch;

(f) to provide a spacer comprising multiple shims connected by links of variable effective length, such that the distance between individual shims is similarly variable;

(g) to provide a spacer whose tray spacing will be visually apparent, to assure the purchaser of the formed dental tray;

(h) to provide a spacer that creates accessible, cleanable reservoir spaces in formed dental trays, such that bacterial plaque and debris are not readily harbored;

(i) to provide a spacer that creates reservoir surfaces in the formed dental trays that do not deteriorate quickly, such as by tearing or oxidation of materials.

Further objects are to provide a spacer that requires minimal time and skill to mount to relevant surfaces of the teeth or dental models, and is economical to use. The foregoing has outlined some of the more pertinent objects of the present invention. These objects should be construed as being merely illustrative of some of the more prominent features and applications of the invention. Many other beneficial results can be obtained by applying the disclosed invention in a different manner or modifying the invention within the scope of the invention. Accordingly further objects, advantages and understanding of the invention may be had by referring to the summary of the invention, and the detailed description, in addition to the scope of the invention defined by the claims taken in conjunction with the accompanying drawings.

DRAWING FIGURES

In the drawings, closely related figures have the same number, but different alphabetic suffixes.

FIGS. 5A to 5F show selected cross-sectional embodiments of spacer shims.

FIG. 6 shows a perspective view of a spacer retained by an elastic loop.

Reference Numerals in Drawings 10 shim

Figure 1:
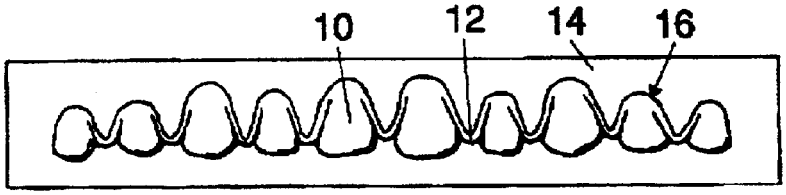
FIG. 1 is an elevational view of the spacer on a backing strip.

12 link
14 backing
16' spacer
20 spacer worm
22 adhesive surface
26 loop anchor
10' shim
12' elastic link
16 spacer
18 model
21 soft tissue spacer
24 loop

SUMMARY

A Dental Tray Spacer is a linked strand of multiple tooth shims for mounting on the surfaces of teeth, or replicas of teeth. The shims cause a reservoir space to form between dental trays and the oral structures, during the fabrication of the dental trays. It should be appreciated by those skilled in the art that the conception and specifics disclosed may be readily utilized as a basis for modifying or designing other structures for carrying out the same purposes of the present invention. It should also be realized by those skilled in the art that such equivalent constructions do not depart form the spirit and scope of the invention as set forth in the appended claims.

DESCRIPTION OF INVENTION—FIGS. 1 TO 6

FIG. 1 shows an elevational view of a preferred embodiment of my dental tray spacer. Individual spacer tooth shim elements, shims 10, are provided in a flat, connected strip, spacer 16. Shims 10 are connected to form spacer 16 by links 12. For spacer 16, the first shim 10 is connected to the first link 12. The first link 12 is connected to the second shim 10. The second shim 10 is connected to the third link 12, and so on, through the final shim 10. The number of shims 10 shown in spacer 16 is typical. However, there could be more, or fewer, shims 10. Spacer 16 is supplied mounted on a backing sheet, backing 14.

The circumference form, or circumferential shape, of each shim 10 approximates the circumferential shape of the corresponding, respective, tooth upon which it is to be mounted. For example, the shim 10 which is to mounted on the surface of the canine tooth has a circumferential shape somewhat resembling that of a canine tooth. The sequential order of the variously shaped shims 10 along spacer 16, corresponds with the typical sequence of teeth. Such sequential grouping of spacers 10 by size and shape makes spacers 16 convenient. However, shims 10 can have a universal circumferential shape, such as an ovoid shape. A selection of sizes enhances the likelihood of adequate coverage of the tooth surfaces. The circumferences of shims 10 are substantially in the plane of the spacer 16 strip.

Generally, the shim 10 circumference will be just slightly smaller than the circumference of the tooth upon which it is to be applied. Thus, a small circumferential area of the tooth surface bordering shim 10 remains uncovered, and unspaced. A dental tray formed over such unspaced circumferential tooth surfaces would rest directly against the circumferential surfaces of the tooth. This creates a sealing effect, enclosing a central, spaced, reservoir area which can retain treatment agents. Similarly, the movement of oral fluids into the circumferential area is somewhat restricted. If unspaced border areas are small, then treatment agents from the spaced dental tray reservoir, will feed to the border adequately enough to treat the border area.

The material from which shims 10 are fabricated is pliable and deformable. Pliability of shims 10 facilitates conforming to the surface contours of the respective mounting teeth. It is preferable that the material also be sufficiently deformable to permit slightly altering the dimensions by pushing the material over the tooth surface. The material may be adequately deformable at room temperature, or its pliability may be increased by heating, or by treating with a solvent. A number of pliable materials are effective. The material cuts readily with scissors or blades to facilitate trimming down the shape where indicated.

Links 12 are connected between shims 10 to facilitate mounting on the teeth. It is preferred that links 12 are comprised of tough, flexible material, continuous with the material of shims 10. However, links 12 may be manufactured from different material than that used for shims 10. Links 12 are of sufficient strength so as to resist inadvertent rupture during routine mounting procedures.

The length of links 12 is sufficient to permit mounting any two linked shims 10 on adjacent, ideally aligned, teeth. Ideally aligned teeth contact one another in the interproximal areas, and the [plane] *planes* of the facial surfaces of the teeth are substantially tangential to the curvature of the dental arch. The length of links 12 required for connected mounting of shims 10 on ideally aligned teeth, is a minimal length.

In the preferred embodiment, the length of links 12 is further sufficient for mounting connected shims 10 on substantially misaligned teeth. Misaligned teeth have gaps, tipping, and rotations, which increase the minimal link 12 length required for mounting shims 10. As such, links 12 are of greater length than required for mounting on ideally aligned teeth.

When mounting spacer 16 on substantially aligned teeth, there remains an unutilized portion of the length of links 12. To prevent inadvertent entanglement, such unutilized length portions of links 12 are weakly connected adjacent to some spacer 16 structure by a separable connection means. The separable connection positions such unutilized lengths of links 12 out of the way of the operator, in reserve. The separable connection is of sufficient strength so as to resist inadvertent separation during routine mounting procedures.

The separate connection is sufficiently weak such that purposeful separation of shims 10 can separate the separable connection without rupture of other spacer 16 structures, such as when mounting links 12 on misaligned teeth. When the separable connection is separated, the utilized length of links 12 is effectively increased. The unutilized length of links 12 can be considered to be effectively decreased, proportionally. As such, adjacent shims 10 thereby remain connected while mounted on teeth with greater, or increased, separation distance. The effective length of links 12 can therefore be considered to be variable.

In the preferred embodiment, the separable connection is a thin membrane of shim 10 material. The thin membrane is weak enough to be purposely torn, but is sufficiently strong to remain intact during routine mounting of spacer 16.

In the preferred embodiment, the separable connection connects the unutilized length portions of links 12 to shim 10. Each link 12 is configured in a bow which point toward the incisal edges of the teeth. However, links 12 may be configured in a bow which point toward the gingival border of the teeth. The unutilized length portions of links 12 are oriented somewhat incisally to gingivally, along the lateral border of shims 10. The utilizable length portion of the link 12 has a substantial mesial to distal orientation, and is located at the apex of the link 12 bow.

Although they are of narrow width relative to shims 10, links 12 have distinctive cross-sectional shapes to minimize entrapment in a formed dental tray. Preferred shapes would be those with carved surfaces, such as cylindrical or ovoid. However, when the rear surfaces of the links are angular or flattened, it is preferable that they exhibit adhesive properties. Thus, they could be pressed into the embrasure crevice, and adhered to the teeth, out of the way of a forming dental tray.

Figure 2:
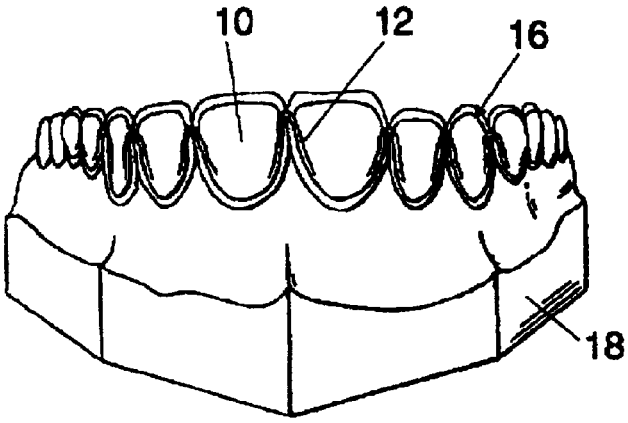
FIG. 2 is a perspective view of the spacer in place on a dental arch model.

FIG. 2 shows a perspective view of spacer 16 mounted on a dental arch model, model 18, ready for dental tray fabrication. However, for intraoral dental tray fabrication techniques, spacer 16 would be mounted on a patient's actual teeth, intraorally. Uncovered circumferential areas are apparent about shims 10.

Figure 3:
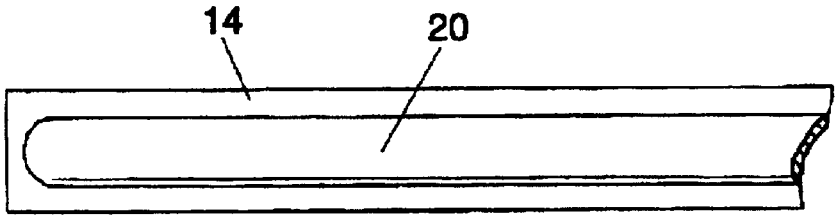
FIG. 3 is an elevational view of the spacer worm variation, on an adhesive backing strip.

FIG. 3 shows a perspective view of an alternative dental tray spacer, a spacer worm 20, as supplied on backing 14. Spacer worm 20 is a continuous spacer strip, whose height is preformed in sizes that approximate the heights of teeth, whose thickness is preformed to create an adequate reservoir space, and whose spacer portions over teeth surfaces are connected continuously by broad linking areas between the teeth, with both spacer areas and link areas having the same height. Spacer worm 20 and backing 14 may be supplied wound on a spool of indefinite length, to be cut to the appropriate length.

Figure 4:
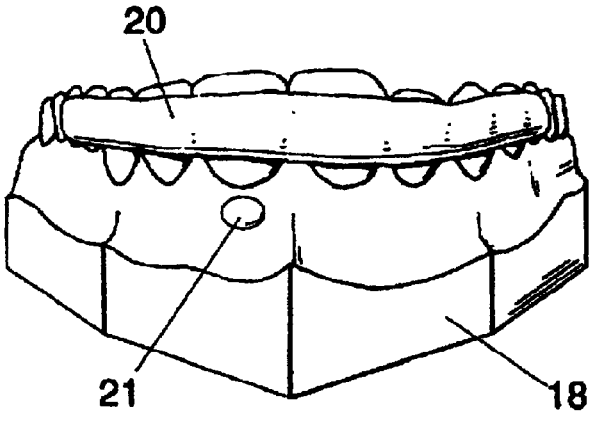
FIG. 4 is a perspective view of the spacer worm variation, and the soft tissue spacer variation, in place on a dental arch model.

FIG. 4 shows a perspective view of spacer worm 20 cut to length and in place on dental arch model 18, ready for dental tray fabrication. The element of spacer worm 20 must be more pliable and deformable than spacer 16, to facilitate mounting on the teeth. It is sufficiently pliable to press into the embrasure crevice between the teeth, despite the breadth of the linking areas. It is sufficiently deformable to permit altering the height dimension, by pushing the element on the tooth surface, such as in areas adjacent to the gingiva. It may be adequately deformable at room temperature, or the pliability may be increased by heating, or by treating with a solvent.

FIG. 4 also shows a perspective view of soft tissue spacer 21 mounted on a selected site on a model 18. Soft tissue spacer 21 may be mounted anywhere on the gingiva, the gingival margin adjacent to the teeth, or the oral mucosal tissue, that the dental tray can extend. Soft tissue spacer 21 will typically be provided in symmetrical shapes and sizes. Soft tissue spacer 21 effectively builds out the surface of the mounting site so that a reservoir space can be created under the forming dental tray. Optional soft tissue spacers 21 with an outer surface color-transfer dye or decal can be convenient for clearly marking the reservoir location in the formed dental tray.

FIGS. 5A to 5F show selected cross-sectional embodiments of shims 10. Cross-sectional shapes shown are 5A lens-shaped, 5B uniform thickness, 5C teardrop, 5D corrugated, 5E concave, and 5F convex. The teardrop, concave, and convex shapes especially facilitate the manual extension of spacer coverage where necessary, such as for longer teeth, or to extend down the root toward the gingiva of teeth where the gums have receded, or for lapping over an incisal edge of a tooth. It is preferred that the depth, or thickness, of any cross-section is less than 1 mm. However, a thickness of 1 mm or greater is also effective. Where possible, spacer 16 edges are tapered to a sharp acute angle, such that they will adhere flush to the teeth, and minimize surface undercuts. This will minimize locking into the dental tray during its fabrication.

Adhesive Surface 22 is the surface of spacer 16 that is to conformably mount onto the teeth. Adhesive Surface 22 is sufficiently pliable to conform closely to the curved, irregular surfaces of teeth or tissue. It is preferred that adhesive surface 22 be supplied exhibiting sufficient adhesive properties to retain spacer 16 on irregular tooth surfaces during the fabrication of the dental tray. However, spacer 16 may be supplied from the manufacturer without adhesive surface 22 exhibiting adhesive properties. As such, the user would apply an adhesive, such as a liquid glue, prior to mounting on model 18.

The adhesive properties of adhesive surface 22 are temporarily and reversibly inhibited, such as with backing 14, or other means of adhesive inhibition. Such inhibition of adhesive surface 22 is reversed prior to mounting on model 18 by removing backing 14. However, inhibition of adhesive surface 22 can be reversed by removing some other protective coating, by heating, by wetting with a solvent, and so on.

FIG. 6 shows a perspective view of a spacer 16' retained by an elastic loop, loop 24. It is preferred that spacer 16' is not simultaneously retained by loop 24 and adhesion. However, simultaneous retention with adhesion is effective. Loop 24 connects the rightmost and leftmost *portions or* shims 10', behind spacer 16'. Loop 24 retained spacer 16' is substantially configured as a closed loop, rather than a flat strip. The circumferences of shim 10' are substantially perpendicular to the plane of such a spacer 16' loop. Loop 24 is shown stretched between the posteriormost teeth on opposing sides of the dental arch of model 18. Stretched thus, loop 24 will typically be suspended a distance above the posterior palate. To prevent suspended loop 24 from becoming locked into a forming dental tray, it is drawn down to the palate by hooking its midpoint on an anchor, loop anchor 26. However, other anchoring devices are effective, or the anchor can be eliminated. Loop anchor 26 is held in its position simply by the weight of model 18.

When spacer 16' is retained by loop 24, it is preferred that the links be comprised of elastic material, forming elastic links 12'. Elastic links 12' may generally be shorter than links 12, and do not necessarily bow between teeth. The lengths of unstretched elastic links 12' approximate the distance between borders of shims 10' mounted on ideally aligned teeth. Elastic Links 12' stretch to accommodate correct positioning of shims 10' during mounting on model 18. As such, elastic links 12' have a variable length. For misaligned teeth, the variable length is utilized by stretching links 12' across the increased distance between the teeth, to position adjacent connected shims 10'.

From the description above, a number of advantages of my dental tray spacer become evident:

(a) Preformed spacers minimize the steps required to form adequate and effective reservoir spaces in formed dental trays.

(b) The spacer can be deformed to compensate for variations in the size, shape and spacing between individual teeth of a dental arch, to facilitate mounting.

(c) The spacer is comprised of multiple shims connected by links with variable effective lengths, such that the distance between individual shims is variable, and may be increased.

(d) Treatment agents are restricted to the reservoir spaces by border seals around the circumferences of the treatment surfaces, and oral fluids are likewise restrained from the treatment surfaces.

(e) Required time and cost is minimized in applying dental tray spacers.

(f) Persons less skilled in dental procedures can apply spacers.

(g) It is visually apparent that the completed dental trays have treatment agent reservoir spaces.

(h) Dental trays formed utilizing the spacers are durable and readily cleanable.

Operation of Invention—FIGS. 1 to 6

Model 18 is free of artifacts, clean and dried. A spacer 16 is selected, whose shims 10 are just slightly smaller than the teeth of model 18, to facilitate formation of a circumferential seal. Spacer 16 is also selected for the most effective cross-sectional shape, shown in FIG. 5, as each shape has unique characteristics for adhering to the teeth. In addition, each shape imparts a unique shape to the subsequently formed reservoir.

Spacer 16 is removed from adhesive backing strip 14, shown in FIG. 1. If spacer 16 is judged to be less pliable than is necessary for mounting, then the pliability may be increased, by exposure to heat, solvent, or such. Spacer 16 is oriented over the teeth of model 18. The first shim 10 is centered over the respective tooth of corresponding shape and position. Shim 10 is mounted by pressing onto the tooth surface, such that shim 10 is conformed to the tooth surface contours. Adhesion of shim 10 to the tooth is thus maximized. If the second respective tooth is aligned with the first tooth, then the second shim 10 in sequence, whose shape corresponds to the second tooth, is likewise centered and applied to the surface. The sequence is repeated for the third shim 10, and so on. Typically, all shims 10 are applied to the teeth in less than 30 seconds.

When a shim 10 is to be applied to an misaligned adjacent tooth, then the utilizable length of the connecting link 12 is increased by separating the separable connection. The separable connection of the link 12 is separated by pulling the shim 10 to be mounted into position over the misaligned tooth. The shim 10 pulls the connected link 12, which in turn separates the separable connection. In the preferred embodiment, the separable membrane connecting link 10 to shim 10 is torn away, increasing the utilizable portion of link 12.

If adjacent teeth are misaligned severely enough so that a link 12 will not stretch between the teeth, despite entirely separating the separable connection, then link 12 can be cut. Links 12 can also be cut to eliminate sequential shims 10, such as at the positions of missing teeth, or to substitute in shims 10 of different size or shape.

When all shims 10 are adhered to respective teeth surfaces, all links 12 are pressed back against the teeth, and between the teeth, so they are out of the way. A mounted spacer 16 is shown in FIG. 2.

Although not necessary for most cases, customizing of shims 10 is performed after application of spacer 16. However, it may be performed prior, or during application. For example, if an individual shim 10 extends beyond the circumference of an unusually shaped tooth on a certain side, then it may be cut to fit. On the other hand, if there is an unusually wide border area of tooth surface extending beyond shim 10, then resin spacer mediums of the art may be added to cover such border areas.

If spacer 16' is retained by loop 24, as shown in FIG. 6, then a spacer 16' with a loop 24 is selected, whose shims 10' are just slightly smaller than the teeth of model 18, and which have the most effective cross-sectional shape. Shims 10' are oriented over the teeth of model 18. Loop 24 is stretched around the posterior ends of the posterior teeth, so that it stretches across the opposite sides of the dental arch, above the palate. Loop 24 is then pulled down to the palatal level, out of the way of forming dental tray material, such as by hooking it on loop anchor 26 *connected to a rear section of the model*. Shims 10 are then centered on each tooth by appropriately stretching elastic links 12'.

Following the application of any spacer 16, or spacer 16', on model 18, a non-stick separating medium is applied to spacer 16, or spacer 16', prior to fabrication of a dental tray. The dental tray stock material pliability is increased, such as by heating. When sufficient pliability is attained, the dental tray stock material is quickly positioned and adapted to cover spacer 16, or spacer 16', and the teeth, such as over model 18. It is preferred that the tray material is made to closely conform to the shape of spacer 16, or spacer 16', by applying a strong vacuum to the under-surface of model 18.

After the dental tray material is made less pliable, such as by sitting at room temperature a short time, the formed dental tray with excess flashing material, is loosened and removed from model 18. If spacer 16, or 16', has become embedded in the dental tray, rather than remaining adhered to model 18, then it must be gently pried free, to avoid breaking links. Used spacers may be discarded, or sterilized for reuse. The dental tray is completed by trimming away extra dental tray material, and assuring that trimmed edges are smooth.

Conclusion, Ramifications, and Scope of Invention

The dental tray spacer of this invention may be quickly adhered to the individual teeth of most dental arch models, in correct order, and with little or no alteration, so that all spacer shapes fit their respective teeth.

Accordingly, the reader will see that the dental tray spacer of this invention can be used to assure the formation of an adequate reservoir space between dental trays and the teeth, and that this can be done in minimal time, with little cost, and without requiring a high level of skill. Most practitioners currently do not provide reservoir spacing under their treatment agent dental trays during fabrication, primarily due to the time and cost of techniques of the art. An efficient spacing technique, such as this, could translate into saving many hours of patient treatment time. For those practitioners that do utilize spacing techniques of the art, the dental tray spacer can save significant time and money, and their patients can be shown the visible reservoir spacing in their trays as assurance that they are receiving efficient treatment.

While my above description contains many specificities, these should not be construed as limitations on the scope of the invention, but rather as an exemplification of some of the presently preferred embodiments thereof. Many other variations are possible. For example, from an elevational view, spacer 16, or spacer 16', could be comprised of symmetrical, ovoid shaped shims 10, rather than tooth shaped. For certain treatments, these would provide adequate reservoir space under the dental tray. Such symmetrical shims 10 could be supplied in a continuous chain, from which a spacer 16, of any desired number of segments, could be cut.

As a second example, spacer 16 could be applied directly to the patient's actual teeth, for intraoral dental tray fabrication techniques, rather than on model 18.

Accordingly, the scope of the invention should be determined, not by the embodiments illustrated, but by the appended claims and their legal equivalents.

I claim:

1. A preformed dental tray spacer means for shimming moldable dental tray material a predetermined distance from surfaces of teeth of a dental arch, or models thereof, comprising a flat, unitary strip of a deformable material substantially elongate in a longitudinal direction and adaptable for rapid shaping and mounting on said surfaces of teeth, or models thereof, said unitary strip comprising a plurality of tooth shim elements connected to each other by means of links, said tooth shim elements having a circumference in the plane of the unitary strip, each said tooth shim element being [comformable] *conformable* overlying surface contours of a tooth, said links being substantially elongate, a portion of said links being substantially elongate in the longitudinal direction of said unitary strip, said links having a sufficient length such that adjacent said tooth shim elements are mountable on adjacent said surfaces of teeth, wherein said circumference of said tooth shim elements is substantially greater than the width of said links.

2. The dental tray spacer means of claim 1, wherein said sufficient length is such that adjacent said tooth shim elements are mountable on adjacent said surfaces of teeth, or models thereof, said surfaces of teeth being substantially misaligned.

3. The dental tray spacer means of claim 1, wherein a portion of said links are further connected to said spacer by means of a separable connection, whereby separating said separable connection increases utilizable said sufficient length, such that adjacent said tooth shim elements are mountable on adjacent said surfaces of teeth, or models thereof, said surfaces of teeth being substantially misaligned, wherein the connected distance between said tooth shim elements is increased.

4. The dental tray spacer means of claim 1, wherein each of said tooth shim elements have distinct circumferential shapes, and said teeth have distinct circumferential shapes, and said circumferential shapes of said tooth shim elements substantially resemble said circumferential shapes of respective said teeth upon which each of said tooth shim elements would be mounted.

5. The dental tray spacer means of claim 1, wherein said tooth shim elements have a surface for mounting against said surfaces of teeth, or models thereof, said surface of said tooth shim element being coated with an adhesive.

6. A preformed dental tray spacer means for shimming moldable dental tray material a predetermined distance from surfaces of teeth of a dental arch, or models thereof, comprising a flat, unitary strip of a deformable material substantially elongate in a longitudinal direction and adaptable for rapid shaping and mounting on said surfaces of teeth, or models thereof, said unitary strip comprising a plurality of tooth shim elements connected to each other by means of links, said tooth shim elements having a circumference in the plane of the unitary strip, each of said tooth shim element being [comformable] *conformable* overlying surface contours of a tooth, said links being substantially elongate, a portion of said links being substantially elongate in the longitudinal direction of said unitary strip, said links having a sufficient length such that adjacent said tooth shim elements are mountable on adjacent said surfaces of teeth, wherein said circumference of said tooth shim elements is substantially greater than the width of said links, wherein a portion of said links are further connected to said spacer by means of a separable connection, whereby separating said separable connection increases utilizable said sufficient length, such that adjacent said tooth shim elements are mountable on adjacent said surfaces of teeth, or models thereof, said surface of teeth being substantially misaligned, wherein the connected distance between said tooth shim elements is increased.

7. The dental tray spacer means of claim 6, wherein said separable connection is a thin membrane.

8. The dental tray spacer means of claim 6, wherein said separable connection connects said links to said tooth shim elements.

9. The dental tray spacer means of claim 6, wherein each of said tooth shim elements have distinct circumferential shapes, and said teeth have distinct circumferential shapes, and said circumferential shapes of said tooth shim elements substantially resemble said circumferential shapes of respective said teeth upon which each of said tooth shim elements would be mounted.

10. The dental tray spacer means of claim 6, wherein said tooth shim elements have a surface for mounting against said surfaces of teeth, or models thereof, said surface of said tooth shim elements being coated with an adhesive.

11. A preformed dental tray spacer means for shimming dental tray material a predetermined distance from preferred surfaces of dental arch model teeth, comprising a plurality of tooth shim elements connected by links of variable length, said links comprised of elastic material, wherein one said link is of sufficient length to stretchingly encompass the circumference of a dental model, such that said tooth shim elements are retainably pulled against said surfaces of said teeth; wherein remaining said links stretch sufficiently to permit rapid positioning of said shims against said surfaces of said teeth.

12. The dental tray spacer means of claim 11, wherein each of said tooth shim elements have distinct circumferential shapes, and said teeth have distinct circumferential shapes, and said circumferential shapes of said tooth shim elements substantially resemble said circumferential shapes of respective said teeth upon which each of said tooth shim elements would be mounted.

13. The dental tray spacer means of claim 11, wherein said tooth shim elements have a surface for mounting against said teeth, said surface being coated with an adhesive.

*14. A method of connecting a dental tray spacer to a dental arch model comprising the acts of:*

*providing a loop that is connected to rightmost and leftmost portions of the spacer; and*

*connecting the loop to a rear section of the model in order to retain the spacer in place.*

*15. A method of connecting a dental tray spacer to a dental arch model according to claim 14 wherein the act of connecting the loop to a rear section of the model includes the act of stretching the loop.*

*16. A method of connecting a dental tray spacer to a dental arch model according to claim 15 wherein the act of stretching the loop includes the act of stretching the loop around the posterior ends of the posterior teeth of the model.*

*17. A method of connecting a dental tray spacer to a dental arch model according to claim 14 and including the act of pulling the loop toward a palatal level.*

*18. A method of connecting a dental tray spacer to a dental arch model according to claim 14 and including the act of applying a non-stick separating medium to the spacer.*

*19. A method of connecting a dental tray spacer to a dental arch model according to claim 14 and including the act of placing the spacer across a multiple number of teeth of the model.*

*20. A method of connecting a dental tray spacer to a dental arch model according to claim 14 wherein the act of connecting the loop to a rear section of the model includes the act of hooking the loop to an anchor.*

*21. A method of connecting a dental tray spacer to a dental arch model according to claim 14 and including the act of retaining the dental tray spacer to the dental arch model with adhesion.*

*22. A method of making a dental tray comprising the acts of:*

*providing an elongated spacer;*

*placing the spacer over facial surfaces of teeth of a dental arch model such that the spacer is generally centered with respect to the center of the dental arch in a mesial-distal direction such that the longitudinal axis of the spacer extends along the length of the arch and such that the spacer extends over more than one tooth of the dental arch model; and*

*forming a sheet of elastomeric tray material over the spacer and the dental arch model to create a dental tray.*

*23. A method of making a dental tray according to claim 22 and including the act of providing an adhesive surface on the spacer for adhesion to the dental arch model.*

*24. A method of making a dental tray according to claim 23 and including the act of removing a backing from the adhesive surface prior to mounting the spacer on the dental arch model.*

*25. A method of making a dental tray according to claim 22 wherein the act of placing the spacer on the dental arch model includes the act of placing the spacer across the tips of papilla of model gingiva between adjacent teeth of the dental arch model.*

*26. A method of making a dental tray according to claim 22 and including the act of pressing the spacer into the embrasure crevice between the teeth.*

*27. A method of making a dental tray according to claim 22 and including the act of freeing the spacer from the tray after the tray is formed.*

*28. A method of making a dental tray comprising the acts of:*

*providing an elongated spacer;*

*placing the spacer over facial surfaces of teeth of a dental arch model such that the spacer is generally centered with respect to the center of the dental arch in a mesial-distal direction;*

*applying a non-stick separating medium to the spacer; and*

*forming a sheet of elastomeric tray material over the spacer and the dental arch model to create a dental tray.*

*29. A method of making a dental tray comprising the acts of:*

*providing an elongated spacer;*

*providing a loop that is connected to rightmost and leftmost portions of the spacer;*

*placing the spacer over facial surfaces of teeth of a dental arch model such that the spacer is generally centered with respect to the center of the dental arch in a mesial-distal direction;*

*connecting the loop to a rear section of the model in order to retain the spacer in place; and*

*forming a sheet of elastomeric tray material over the spacer and the dental arch model to create a dental tray.*

*30. A preformed dental tray spacer for shimming moldable dental tray material a predetermined distance away from surfaces of teeth of a dental arch or models thereof comprising a unitary, elongated strip of material having an adhesive surface, and a backing removably connected to the adhesive surface, wherein the spacer has edges that are tapered to an acute angle.*

*31. A preformed dental tray spacer according to claim 30 wherein the adhesive surface is sufficiently pliable to conform closely to curved, irregular surfaces of teeth of tissue.*

*32. A preformed dental tray spacer for shimming moldable dental tray material a predetermined distance away from surfaces of a dental arch or models thereof comprising a unitary, elongated strip of material having an adhesive surface, and a backing removably connected to the adhesive surface, wherein the spacer has a rightmost portion and a leftmost portion, and wherein the spacer includes a loop connected to the rightmost portion and the leftmost portion.*

*33. A preformed dental tray spacer according to claim 32 wherein the loop is stretchable.*

*34. An assembly comprising:*

*a dental arch model;*

*a dental tray spacer for shimming moldable dental tray material a predetermined distance away from surfaces of teeth of the model, the spacer comprising a unitary, elongated strip of material having an adhesive surface in contact with the model and extending along the length of the arch, wherein the spacer has edges that are tapered to an acute angle; and*

*a non-stick separating medium applied to the spacer for contact with the tray material.*

* * * * *

UNITED STATES PATENT AND TRADEMARK OFFICE

CERTIFICATE OF CORRECTION

PATENT NO. : RE 38,811 E
DATED : October 4, 2005
INVENTOR(S) : Knutson, Eric J.

It is certified that error appears in the above-identified patent and that said Letters Patent is hereby corrected as shown below:

Column 11,
Line 7, after “strip, each” delete “of”.
Line 8, delete “comformable” and insert -- conformable --.
Line 20, delete “surface” and insert -- surfaces --.

Column 14,
Line 3, after “surfaces of” insert -- teeth of --.

Signed and Sealed this

Tenth Day of January, 2006

JON W. DUDAS
*Director of the United States Patent and Trademark Office*